US 12,329,326 B1

(12) United States Patent
Fan et al.

(10) Patent No.: US 12,329,326 B1
(45) Date of Patent: Jun. 17, 2025

(54) TOWEL HEATING DEVICE

(71) Applicant: Guangzhou Hansong Electric Technology Co., Limited, Guangdong (CN)

(72) Inventors: Zhilin Fan, Guangdong (CN); Zhenji Lin, Guangdong (CN)

(73) Assignee: Guangzhou Hansong Electric Technology Co., Limited, Guangzhou (CN)

( * ) Notice: Subject to any disclaimer, the term of this patent is extended or adjusted under 35 U.S.C. 154(b) by 0 days.

(21) Appl. No.: 18/763,632

(22) Filed: Jul. 3, 2024

(30) Foreign Application Priority Data

Mar. 7, 2024 (CN) .......................... 202410260988.9
Mar. 7, 2024 (CN) .......................... 202420441375.0

(51) Int. Cl.
*A47K 10/06* (2006.01)

(52) U.S. Cl.
CPC .................................. *A47K 10/06* (2013.01)

(58) Field of Classification Search
CPC ........ A47K 10/00; A47K 10/06; A47K 10/16; A47K 10/24; A45C 15/00; A45C 3/001; A45C 7/0095; H05B 3/34
USPC ....................................................... 219/521
See application file for complete search history.

(56) References Cited

U.S. PATENT DOCUMENTS

| | | | | |
|---|---|---|---|---|
| 3,160,482 A * | 12/1964 | Foote | ..................... | D06F 58/14 392/435 |
| 3,190,012 A * | 6/1965 | Gray | ..................... | D06F 58/14 34/91 |
| 3,280,477 A * | 10/1966 | Rawlins | ..................... | D06F 58/14 D6/315 |
| 3,577,650 A * | 5/1971 | Brahm | ..................... | D06F 58/14 219/400 |
| 5,478,138 A * | 12/1995 | Yu | ..................... | A47C 4/14 297/461 |
| 6,433,317 B1 * | 8/2002 | Arx | ..................... | H05B 3/28 219/544 |
| 2004/0093758 A1 * | 5/2004 | Miller | ..................... | D06F 58/14 34/201 |
| 2013/0153560 A1 * | 6/2013 | Lev | ..................... | H05B 3/34 219/385 |

* cited by examiner

*Primary Examiner* — Sang Y Paik

(57) ABSTRACT

A foldable towel heating device includes: two rigid shells; a flexible connection member; two foldable brackets; and a heating assembly. The flexible connection member is connected with the two rigid shells. The flexible connection member and the two rigid shells cooperatively enclose a receiving chamber. Any one of the two rigid shells and the flexible connection member defines an opening communicating with the receiving chamber. Two foldable brackets are connected with the two rigid shells. When the two foldable brackets are being folded/unfolded, the two rigid shells are driven to move to approach/away from each other correspondingly, the flexible connection member is driven to be folded/unfolded correspondingly. The heating assembly is disposed in the two rigid shells and/or the flexible connection member. The heating assembly is configured to heat the receiving chamber.

18 Claims, 14 Drawing Sheets

TOWEL HEATING DEVICE

CROSS REFERENCE TO RELATED APPLICATIONS

The present application claims priorities of the Chinese patent application No. 202410260988.9, filed on Mar. 7, 2024 and the Chinese utility model application No. 202420441375.0, filed on Mar. 7, 2024 and contents of which are incorporated herein by their entireties.

TECHNICAL FIELD

The present disclosure relates to the field of towel heating devices, and in particular to a towel heating device.

BACKGROUND

A towel heating device is substantially configured to receive a towel and to heat the towel. The towel heating device may quickly heat the towel to reach a proper temperature, enabling a user to feel a more comfortable temperature when taking a bath or washing the face.

A shell of the towel heating device in the art usually has a fixed structure. The shell of the towel heating device occupies a large space and cannot be deformed, such that the towel heating device may not be transported and stored easily.

SUMMARY OF THE DISCLOSURE

The present disclosure a foldable towel heating device including: two rigid shells; a flexible connection member; two foldable brackets; a heating assembly. The flexible connection member are connected with the two rigid shells. The flexible connection member and the two rigid shells cooperatively enclose a receiving chamber; any one of the two rigid shells and the flexible connection member defines an opening communicating with the receiving chamber. Two foldable brackets are connected with the two rigid shells. When the two foldable brackets are being folded, the two rigid shells are driven to move to approach each other, the flexible connection member is driven to be folded correspondingly; and when the two foldable brackets are being unfolded, the two rigid shells are driven to move away from each other, the flexible connection member is driven to be unfolded correspondingly. The heating assembly is disposed in the two rigid shells and/or the flexible connection member, wherein the heating assembly is configured to heat the receiving chamber.

BRIEF DESCRIPTION OF THE DRAWINGS

In order to more clearly illustrate the technical solutions in the embodiments of the present disclosure or in the art, the accompanying drawings for describing the embodiments of the present disclosure or in the art will be briefly introduced in the following. Obviously, that the following accompanying drawings show only some of the embodiments of the present disclosure. Any ordinary skilled person in the art may obtain other accompanying drawings based on the following drawings without making any creative work.

REFERENCE NUMERALS IN THE DRAWINGS

Figure 1:
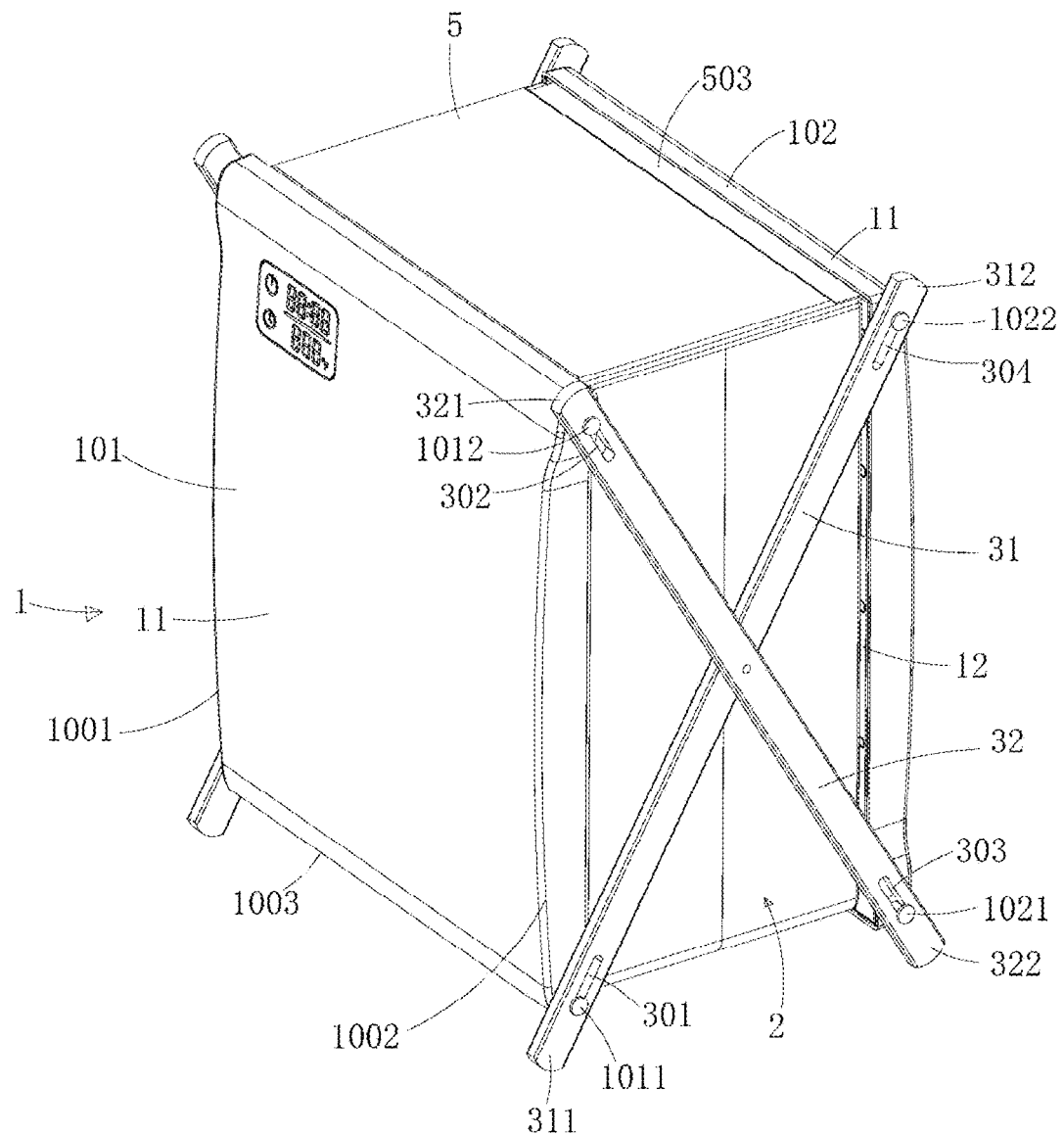
FIG. 1 is a perspective view of a towel heating device according to an embodiment of the present disclosure, in which a foldable bracket is in an unfolding state, and the foldable bracket has a first slide slot, a second slide slot, a third slide slot, and a fourth slide slot.

Rigid shell 1, shell body 11, cavity 111, first fixation frame 12, second fixation frame 13, first positioning post 112, second positioning post 113, third positioning post 114, first fixation rod 121, second fixation rod 131, first clamping protrusion 1311, second clamping protrusion 1141, wire through-slot 122, limiting tab 132, front shell 101, rear shell 102, first connection shaft 1011, second connection shaft 1012, third connection shaft 1021, fourth connection shaft 1022, left end of the rigid shell 1001, right end of the rigid shell 1002, bottom of the rigid shell 1003, inner side of the first fixation frame 1201;

Flexible connection member 2, first receiving bag 21, first heat-insulation layer 22, first fabric sheet 211, first connection portion 201, flexible bottom plate 202, flexible side plate 203, bottom of the flexible connection member 2001, and side of the first heat-insulation layer facing the receiving chamber 2201;

Foldable bracket 3, first support rod 31, second support rod 32, first end of the first support rod 311, second end of the first support rod 312, first end of the second support rod 321, second end of the second support rod 322, first slide slot 301, second slide slot 302, third slide slot 303, fourth slide slot 304;

Heating assembly 4, heating plate 41, flexible heating sheet 42, control board 43, heat-conducting plate 411, electric wire plate 412, bottom heating sheet 421, side heating sheet 422, first conducting wire 401, second conducting wire 402, edge of the heating plate 4101, side of the heating plate 4102, side of the heat-conducting plate facing the cavity 4111, side of the control board 431;

Top cover 5, first end of the top cover 501, second end of the top cover 502, second connection portion 503, second receiving bag 51, second heat-insulation layer 52, second fabric sheet 511, edge of the second receiving bag 5101;

Receiving chamber 6, bottom wall of the receiving chamber 61, side wall of the receiving chamber 61;

Opening 7;

Bolt 8.

DETAILED DESCRIPTION

Unless otherwise defined, all technical and scientific terms used herein have the same meaning as commonly understood by any ordinary skilled person in the art. Terms used herein in the specification of the present disclosure are used only for the purpose of describing specific embodiments and are not intended to limit the present disclosure. The terms "include", "have" and any variations thereof in the specification, claims, and accompanying drawings of the present disclosure are intended to cover non-exclusive inclusion. The terms "first", "second", and so on in the specification, claims, and the accompanying drawings of the present disclosure are used to distinguish different objects and are not intended to describe a particular order.

Reference to "embodiment" herein implies that particular features, structures, or properties described in an embodiment may be included in at least one embodiment of the present disclosure. The presence of the term at various sections in the specification does not necessarily refer to a same embodiment, nor a separate or an alternative embodiment that is mutually exclusive of other embodiments. Any ordinary skilled person in the art shall understand, explicitly and implicitly, that the embodiments described herein may be combined with other embodiments.

In order to enable any ordinary skilled person in the art to better understand the embodiments of the present disclosure, technical solutions in the embodiments of the present disclosure will be clearly and completely described below by referring to the accompanying drawings.

As shown in FIGS. 1 to 14, the present disclosure provides a towel heating device, including two rigid shells 1, a flexible connection member 2, at least one foldable bracket 3, and a heating assembly 4. Folding or unfolding the foldable bracket 3 drives the two rigid shells 1 to move towards or away from each other and drives the flexible connection member 2 to be correspondingly folded or unfolded. Therefore, the towel heating device herein may be a foldable or folding towel heating device.

The two rigid shells 1 are arranged parallel to each other. Each rigid shell 1 includes a shell body 11, a first fixation frame 12 and a second fixation frame 13. The shell body 11 defines a cavity 111. The second fixation frame 13 is disposed at an inner side 1201 of the first fixation frame 12. The first fixation frame 12 and the second fixation frame 13 are both connected to the shell body 1 and are received in the cavity 111. The inner side 1201 of the first fixation frame 12 refers to a space surrounded by the first fixation frame 12. To be noted that, the two rigid shells 1 may cooperatively form any shape, such as cylindrical, squared, polygonal, and so on. For example, when the two rigid shells 1 form a cylindrical structure, the towel heating device in the present disclosure may be a foldable or folding towel warmer bucket.

Each of two sides of the flexible connection member 2 is arranged with a first connection portion 201. The two first connection portions 201 are fixed to the two rigid shell bodies 1, respectively. Specifically, each first connection portion 201 firstly extends through a gap between the first fixation frame 12 and the second fixation frame 13, and is then clamped between the first fixation frame 12 and the shell body 11. The flexible connection member 2 is arranged to connect the two rigid shells 1 to each other, and the flexible connection member 2 and the two rigid shells 1 cooperatively enclose a receiving chamber 6. The receiving chamber 6 has an opening 7. The opening 7 may be defined in either one of the two rigid shells 1 or in the flexible connection member 2. The opening 7 is configured to enable a user to place a towel into the receiving chamber 6.

Figure 14:
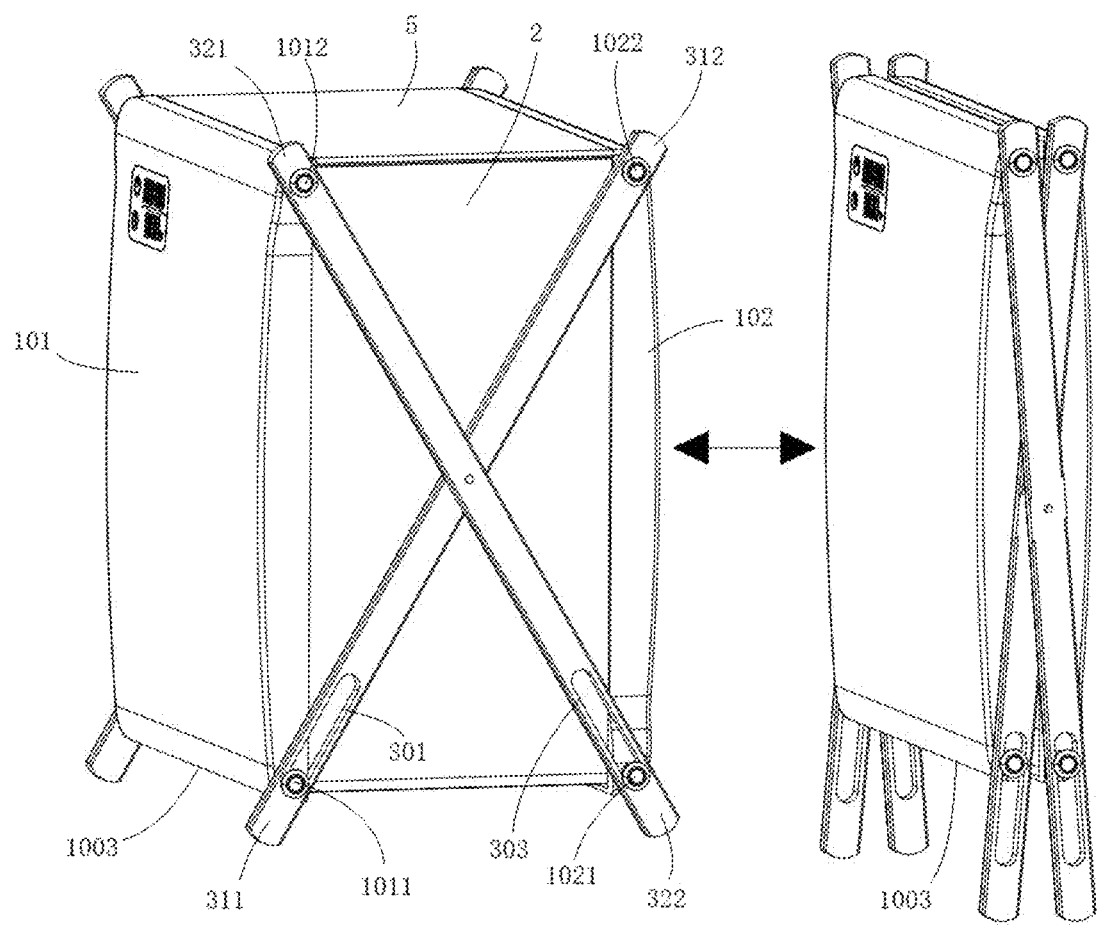
FIG. 14 is another perspective view of the towel heating device according to an embodiment of the present disclosure, in which the foldable bracket is in the unfolding state and in the folding state, and the foldable bracket has the first slide slot and the third slide slot.

The at least one foldable bracket 3 is connected to the two rigid shells 1. Each foldable bracket 3 may be a scissor-type structure, a folding plate, and so on. As shown in FIGS. 1 and 14, when the foldable bracket 3 is being folded, the two rigid shells 1 are driven to move to approach each other, and the flexible connection member 2 is folded correspondingly. As shown in FIG. 14, when the foldable bracket 3 is being unfolded, the two rigid shells 1 are driven to move away from each other, and the flexible connection member 2 is unfolded correspondingly. In addition, in order to improve balance and stability of mutual movement between the two rigid shells 1, in the present embodiment, two foldable brackets 3 are arranged, and each of the two foldable brackets 3 is in a scissor form. The two foldable brackets 3 are symmetrically disposed at a left end 1001 and a right end 1002 of the rigid shells 1, such that the two rigid shells 1 are enabled to move towards each other more stably and reliably. Of course, in other embodiments, only one foldable bracket 3 is arranged to connect the two rigid shells 1 to each other, and the two rigid shells 1 can still be driven to move towards each other. The only difference is reflected in the stability of the movement between the two rigid shells 1. This type of embodiment is not shown in the accompanying drawings.

The heating assembly 4 may be disposed on any of the rigid shells 1 and/or the flexible connection member 2. When the heating assembly 4 is disposed on the rigid shell 1, the second fixation frame 13 is configured to fix the heating assembly 4. The user may place the towel into the receiving chamber 6 from the opening 7, the heating assembly 4, which is disposed in the towel heating device, is configured to heat the receiving chamber 6 and the towel received therein. In addition, the user may take the foldable bracket 3 to drive the two rigid shells 1 to move to approach or away from each other. Since the flexible connection member 2 has a deforming capability, the approaching movement between the two rigid shells 1 may not be blocked by the flexible connection member 2. Therefore, the towel heating device may be folded and unfolded, and can be stored and transported easily.

Connection between the flexible connection member 2 and the two rigid shells 1 is as follows.

Figure 4:
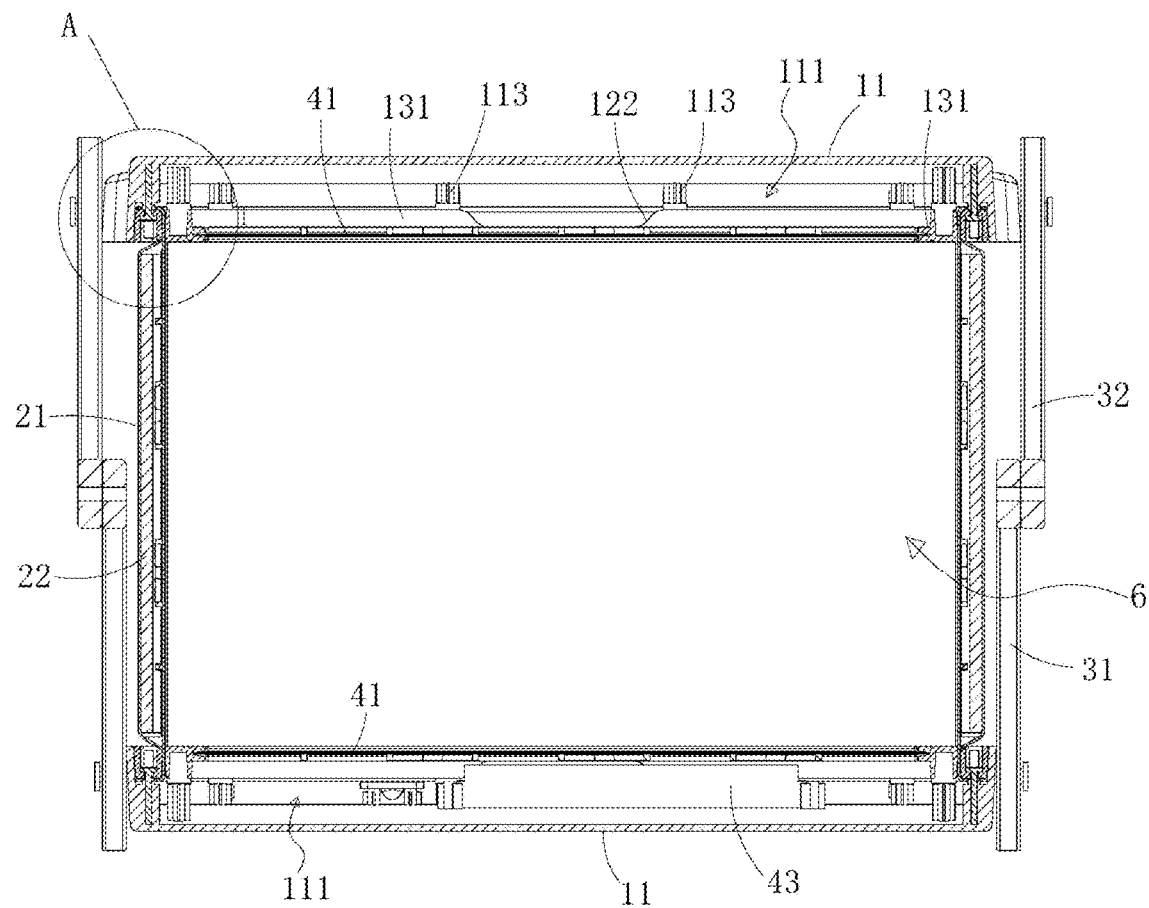
FIG. 4 is a cross-sectional view of the towel heating device according to an embodiment of the present disclosure.
Figure 5:
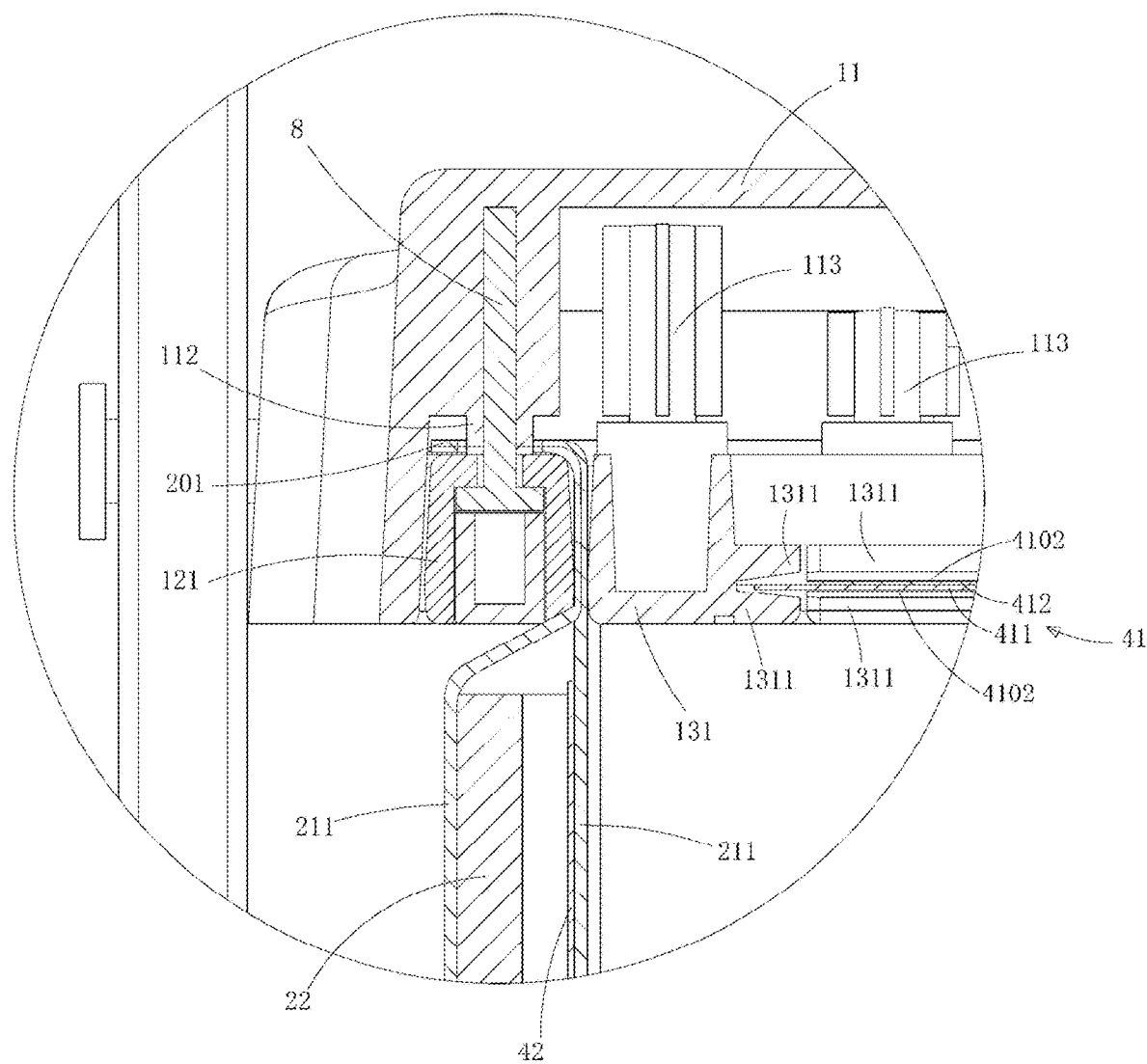
FIG. 5 is an enlarged view of a portion A shown in FIG. 4.
Figure 6:
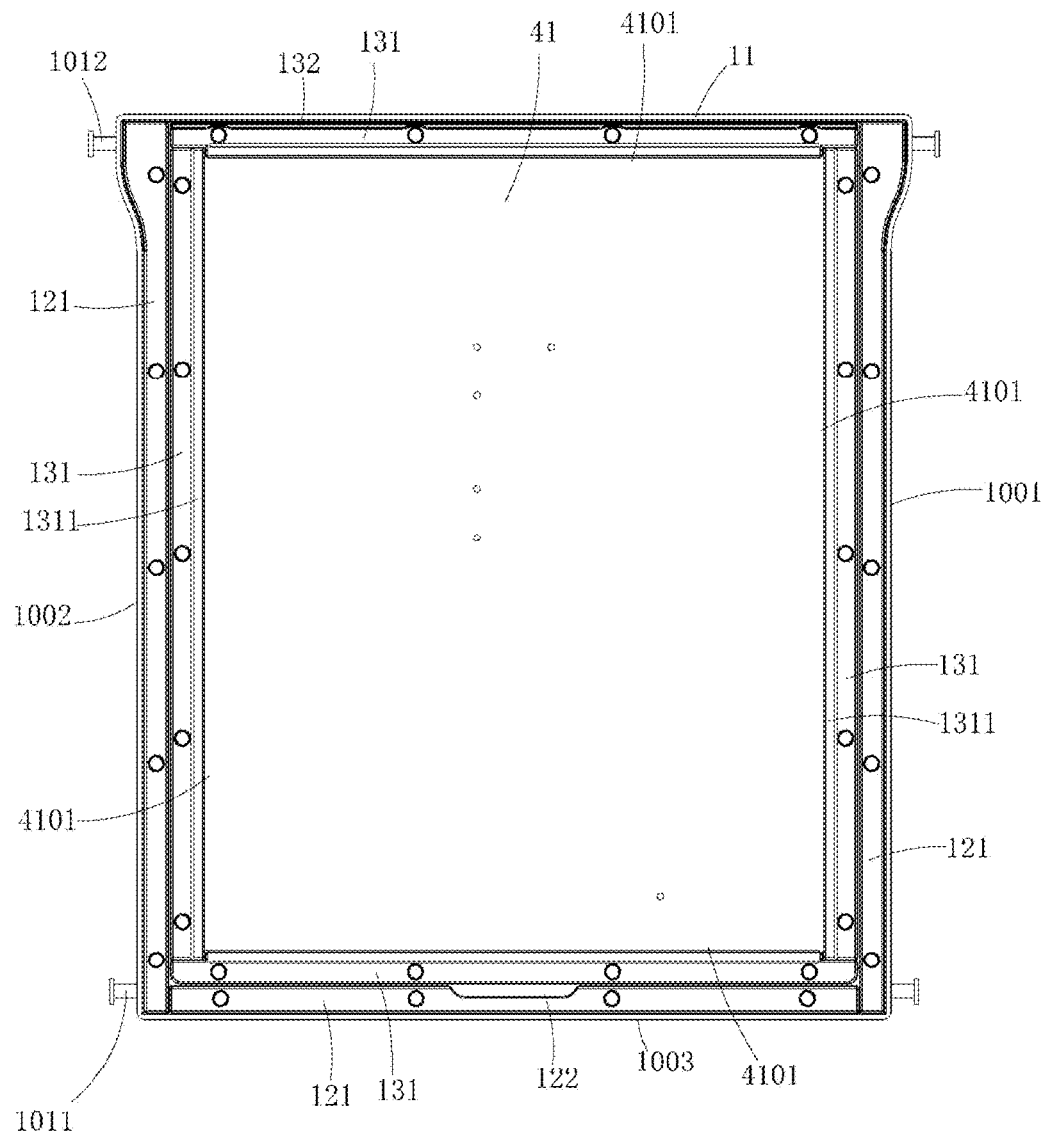
FIG. 6 is a schematic view of connection between a rigid shell and a heating plate according to an embodiment of the present disclosure.
Figure 7:
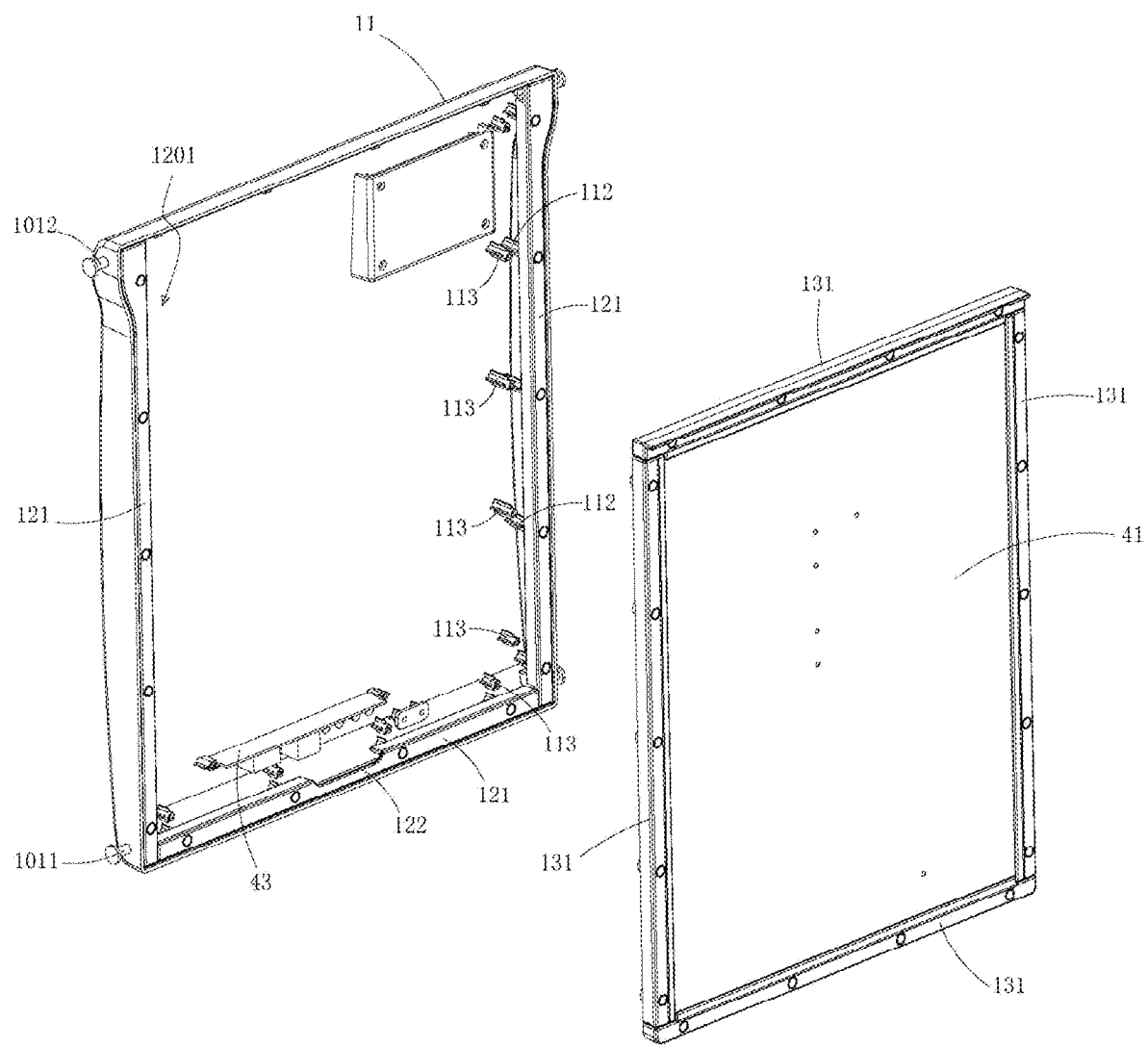
FIG. 7 is a schematic view of connection between a shell body, a first fixation frame, a second fixation frame, and the heating plate according to an embodiment of the present disclosure.
Figure 12:
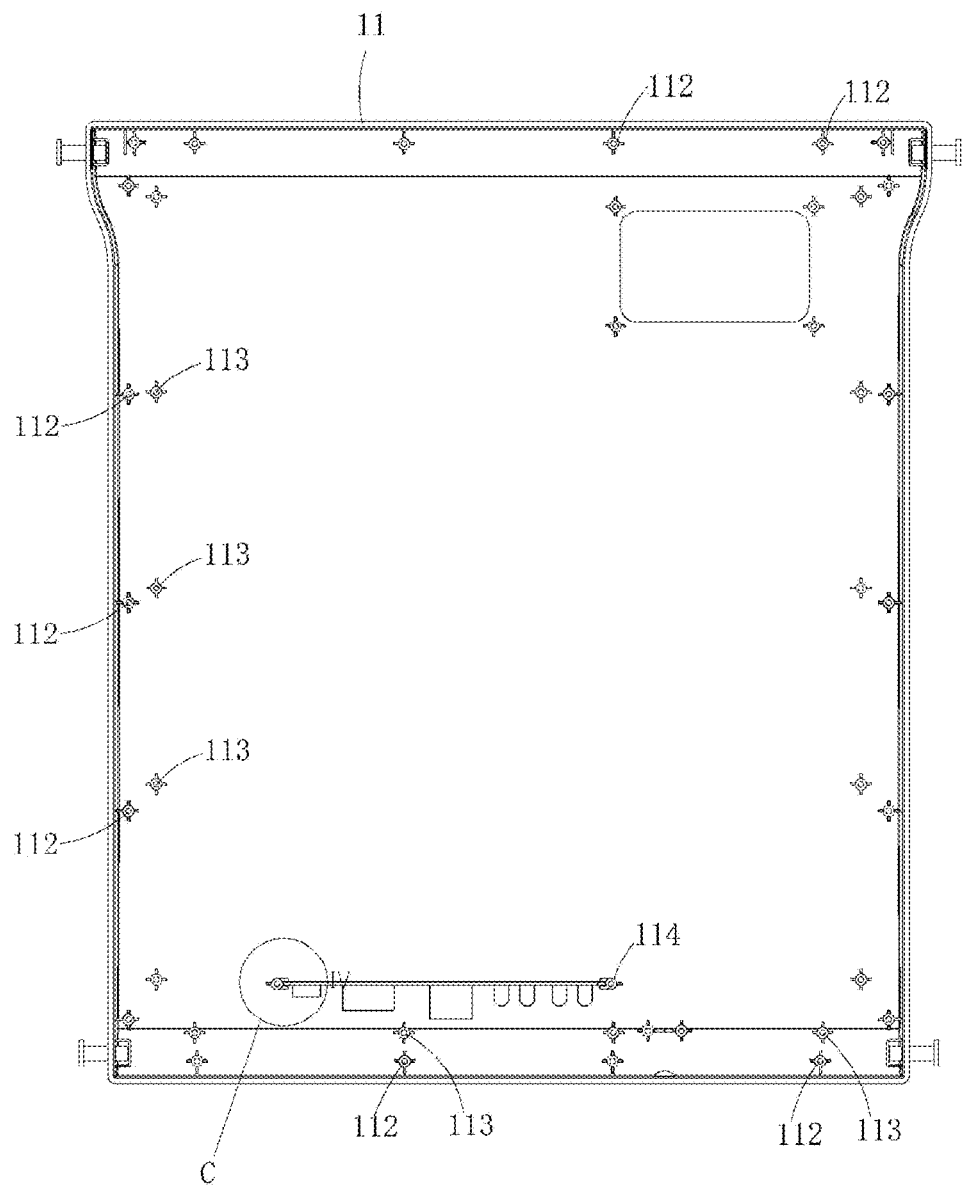
FIG. 12 shows distribution of a first positioning post, a second positioning post, and a third positioning post in a cavity according to an embodiment of the present disclosure.

As shown in FIGS. 4, 5, 12, a plurality of first positioning posts 112 are arranged on the shell body 11. Each first positioning post 112 extends through the respective first connection portion 201. The first fixation frame 12 is fastened to the plurality of first positioning posts 112 by bolts 8. Specifically, when one first connection portion 201 is connected with one rigid shell 1, the first positioning posts 112 on the rigid shell 1 extend through the first connection portion 201, and subsequently, the first fixation frame 12 is brought to approach the shell body 11. The first positioning posts 112 are aligned to corresponding bolt holes defined in the first fixation frame 12. At last, the bolts 8 are arranged to fasten the first fixation frame 12 to the first positioning posts 112. In this way, the first connection portion 201 is clamped between the shell body 11 of the rigid shell 1 and the first fixation frame 12. The connection between the flexible connection member 2 and the rigid shell 1 is more secure. Accordingly, two first connection portions 201 of the flexible connection member 2 are fastened successively by following the above method, such that the connection between the flexible connection member 2 and the two rigid shells 1 is achieved. In this process, the first positioning posts 112 are used to position the first connection portion 201 with respect to the first fixation frame 12, and the bolts 8 are used to achieve the fastening and fixation between the first connection portion 201 and the first fixation frame 12.

Figure 2:
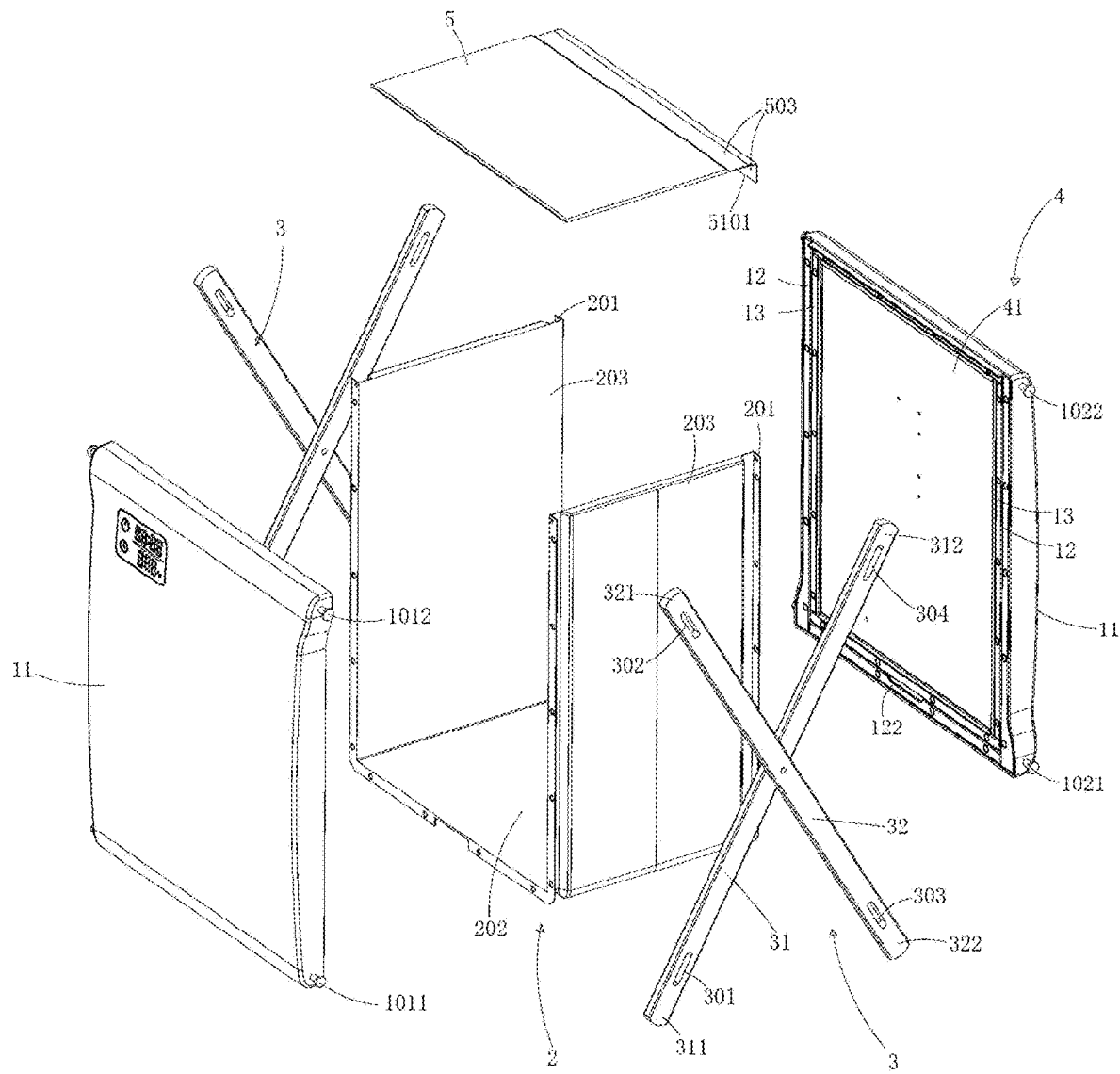
FIG. 2 is an exploded view of the towel heating device according to an embodiment of the present disclosure.
Figure 3:
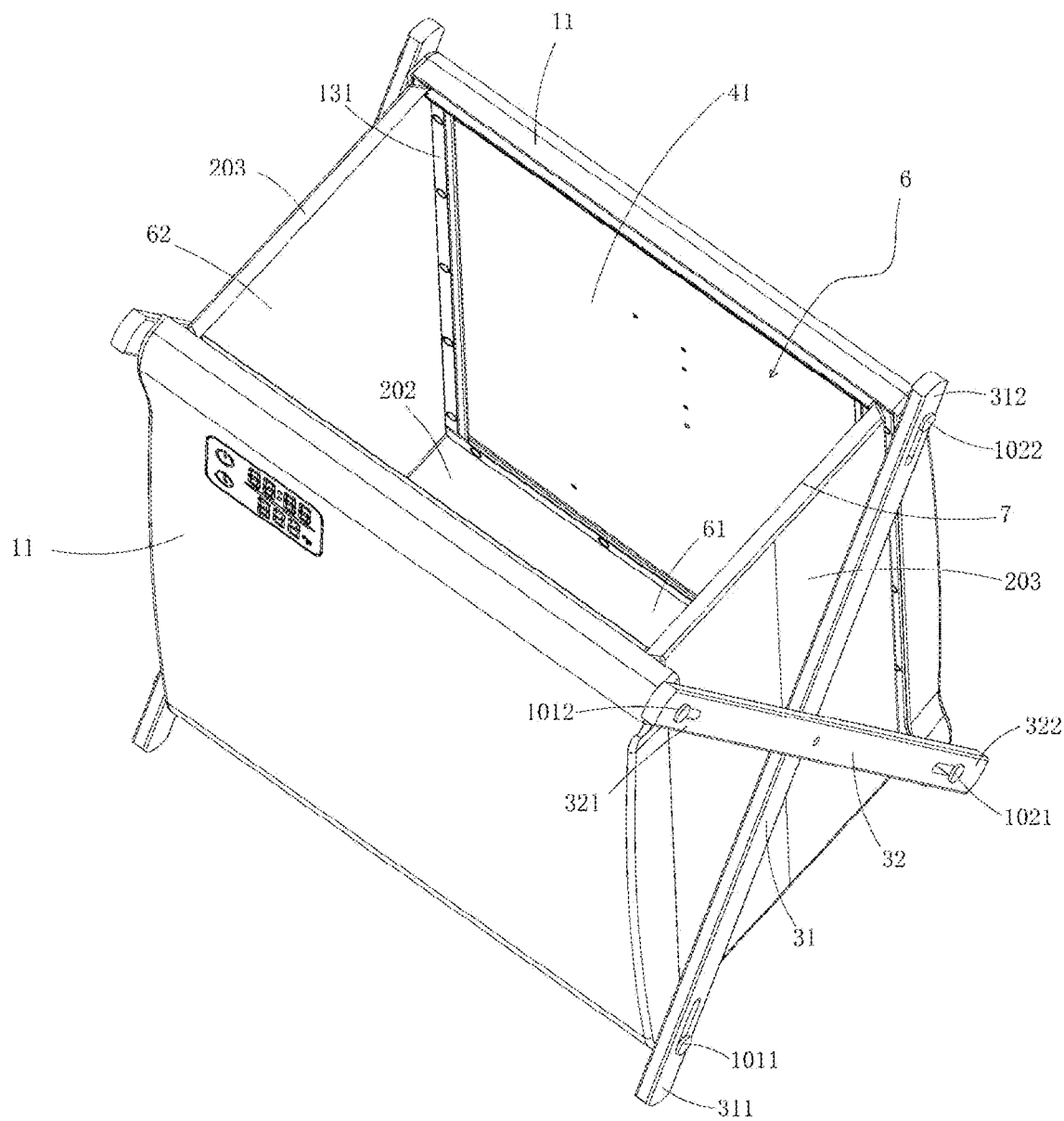
FIG. 3 is a schematic view of a receiving chamber and an opening of the towel heating device according to an embodiment of the present disclosure.

In addition, as shown in FIG. 2, the flexible connection member 2 includes a flexible bottom plate 202 and two flexible side plates 203. The flexible bottom plate 202 and the two flexible side plates 203 are integrally formed as a one-piece structure. The flexible bottom plate 202 and the two flexible side plates 203 cooperatively form a "U"-shaped structure, such that a bottom 61 and four sides 62 of the receiving chamber 6 are closed, and the only opening 7 is formed at a top of the U-shaped flexible connection member 2. The first connection portion 201 is extended along and distributed at an edge of each of the two flexible side plates 203 and the flexible bottom plates 202. That is, the first connection portion 201 extends along a length direction of the flexible connection member 2. In order to facilitate the connecting process between the flexible connection member 2 and the rigid shell 1, the first fixation frame 12 is formed by three first fixation rods 121 sequentially connected to each other from end to end. The three first fixation rods 121 are configured to fix two first connection portions 201 arranged on the two flexible side plates 203 and one first connection portion 201 arranged on the flexible bottom plate 202, respectively.

Further, in an embodiment, the heating assembly 4 is disposed on only the two rigid shells 1. In the present embodiment, the heating assembly 4 includes two heating plates 41 and a control board 43. The two heating plates 41 are electrically connected to the control board 43. The two heating plates 41 are mounted on two second fixation frames 13 of the two rigid shells 1, respectively. The control board 43 is mounted on the shell body 11 of either one of the two rigid shells 1. The control board 43 is a PCB board.

In another embodiment of the present disclosure, the heating assembly 4 is disposed on the two rigid shells 1 and the flexible connection member 2. In the present embodiment, the heating assembly 4 includes two heating plates 41, a flexible heating sheet 42, and a control board 43. The two heating plates 41 and the flexible heating sheet 42 are electrically connected to the control board 43. The two heating plates 41 are mounted on the two second fixation frames 13 of the two rigid shells 1, respectively. The flexible heating sheet 42 is mounted in the flexible connection member 2. The control board 43 is mounted in the cavity 111 of either one of the two rigid shells 1. The control board 43 is the PCB board.

Mounting of the heating plate 41 on the second fixation frame 13 is as shown in FIGS. 6, 7, 8, and 12.

A plurality of second positioning posts 113 are arrnaged on each shell body 11. The plurality of second positioning posts 113 are inserted into the second fixation frame 13. Bolts 8 may further be arranged to fasten the second fixation frame 13 to the second positioning posts 113. The heating plate 41 is mounted at a middle of the second fixation frame 13. In this way, mounting of the flexible connection member 2 and mounting of the heating assembly 4 are performed separately from each other. Therefore, the mounting can be performed conveniently, and connection stability can be ensured. In this process, the second positioning posts 113 are configured to position the second fixation frame 13, and the bolts 8 are configured to fasten and fix the first fixation frame 12.

In addition, the heating plate 41 may be rectangular. The second fixation frame 13 is an enclosed structure formed by four second fixation rods 131 successively connected to each other from end to end. The four second fixation rods 131 cooperatively clamp one heating plate 41. Each second fixation rod 131 is arranged with two first clamping protrusions 1311. The two first clamping protrusions 1311 abut against two side surfaces 4102 of the heating plate 41, respectively. The two first clamping protrusions 1311 cooperatively clamp one heating plate 41. The four second fixation rods 131 are disposed at and clamp four edges 4101 of the heating plate 41, respectively. In this way, the four edges 4101 of the heating plate 41 are completely wrapped in the second fixation frame 13. Further, the second fixation frame 13 is mounted to the shell body 11. In this way, the fixation of the heating plate 41 is more convenient and reliable. On the other hand, since the heating plate 41 generates heat and is at a high temperature when operating, in the present embodiment, the second fixation frame 13 is made of plastic material that is resistant to high temperatures and is flame retardant; and the shell body 11 is made of any ordinary plastic material at a lower cost.

Figure 8:
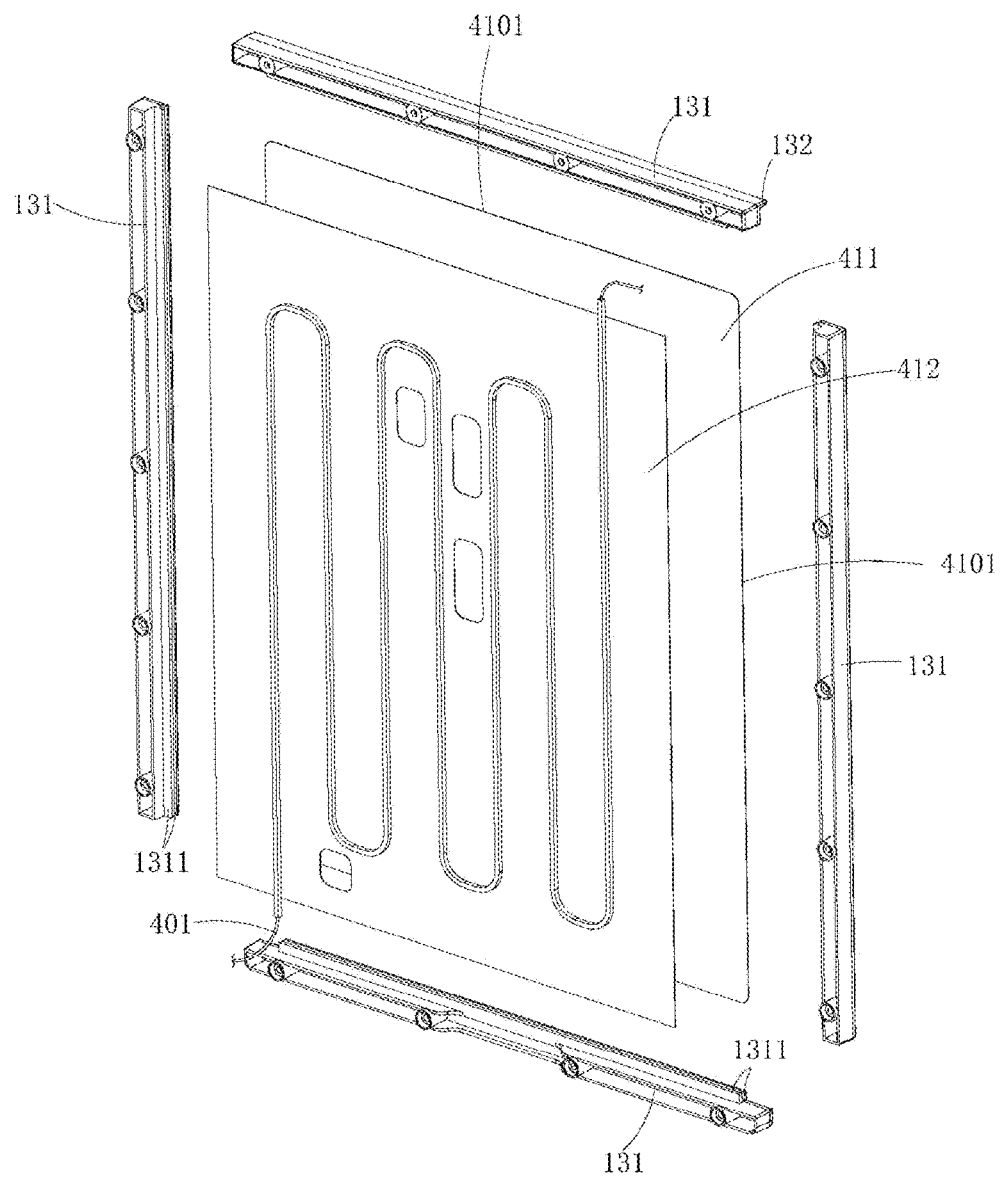
FIG. 8 is an exploded view of the second fixation frame and the heating plate according to an embodiment of the present disclosure.
Figure 9:
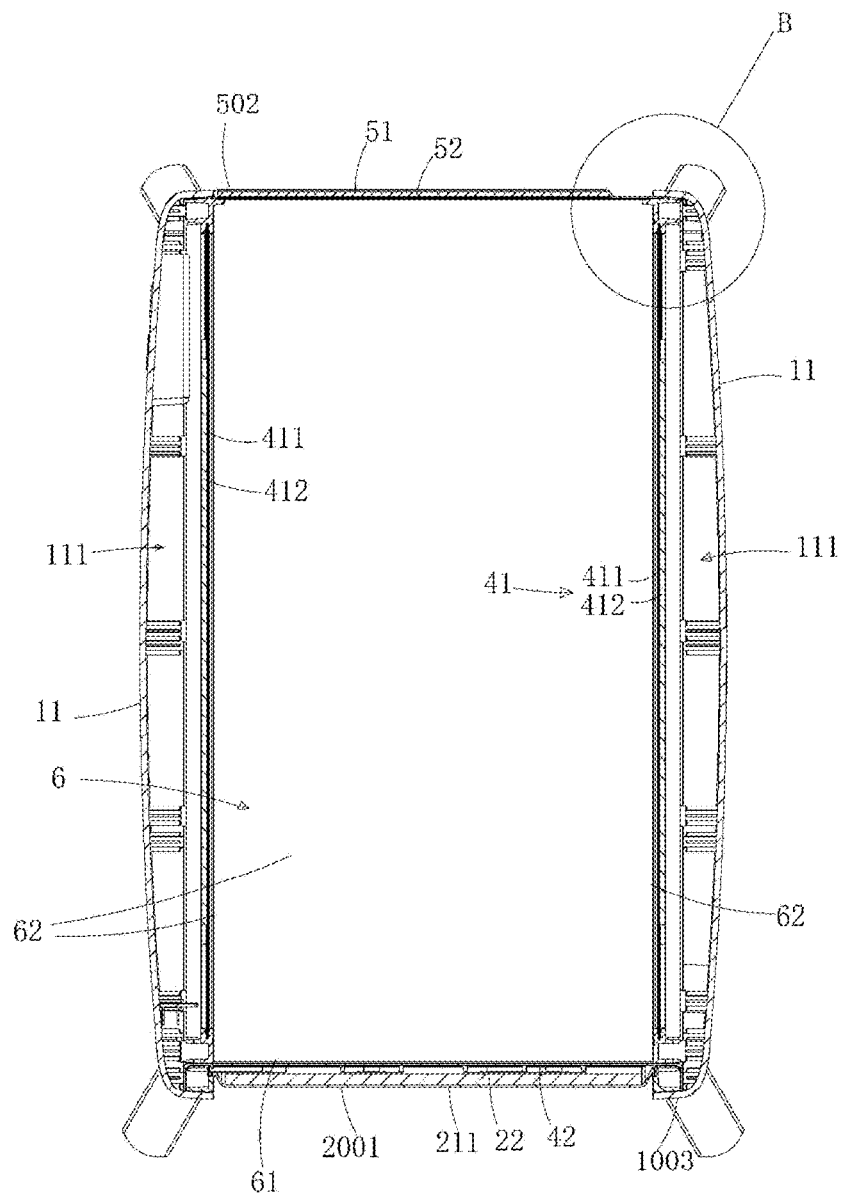
FIG. 9 is a cross-sectional view of the towel heating device according to an embodiment of the present disclosure, in which a bottom wall and another three side walls of the receiving chamber are shown.
Figure 10:
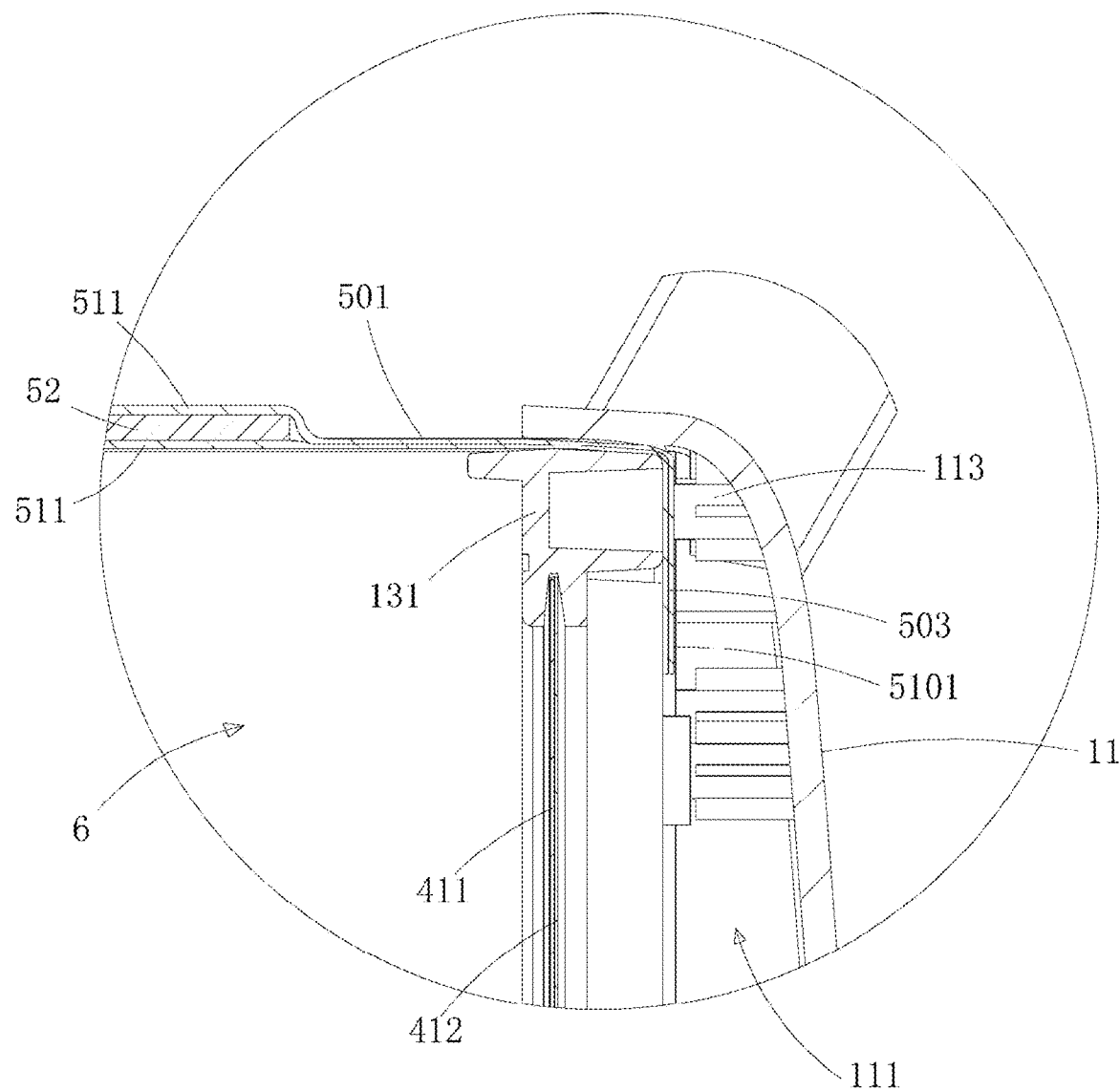
FIG. 10 is an enlarged view of a portion B shown in FIG. 9.

Specific structure of the heating plate 41 is as shown in FIG. 8.

The heating plate 41 includes a heat-conducting plate 411 and an electric wire plate 412. The electric wire plate 412 is electrically connected to the control board 43. The heat-conducting plate 411 is mounted in the middle of the second fixation frame 13.

In addition, since the electric wire plate 412 generates heat to reach a high temperature when operating, the user may be burned if direct contacting the electric wire plate 412. The electric wire plate 412 is adhered, by a double-sided adhesive, to a side 4111 of the heat-conducting plate 411 facing the cavity 111. In this way, the electric wire plate 412 is prevented from being directly exposed to the receiving chamber 6, and the service life of the electric wire plate 412 is extended. The heat-conducting plate 411 is a steel plate with a zinc layer plated on a surface thereof. The heat generated by the electric wire plate 412 is conducted into the receiving chamber 6 through the heat-conducting plate 411. Moreover, the heat-conducting plate 411 has good corrosion resistance, and a service life of the heat-conducting plate 411 in a humid environment may be improved.

Each of the two heating plates 41 is electrically connected to the control board 43 by a first wire 401. A bottom of each of the two first fixation frames 12 defines a wire through-slot 122 extending through the bottom. The wire through-slot 122 is defined to enable the first wire 401 to pass through. In addition, the first wire 401 may further arranged to extend through the flexible connection member 2 if desired.

Figure 11:
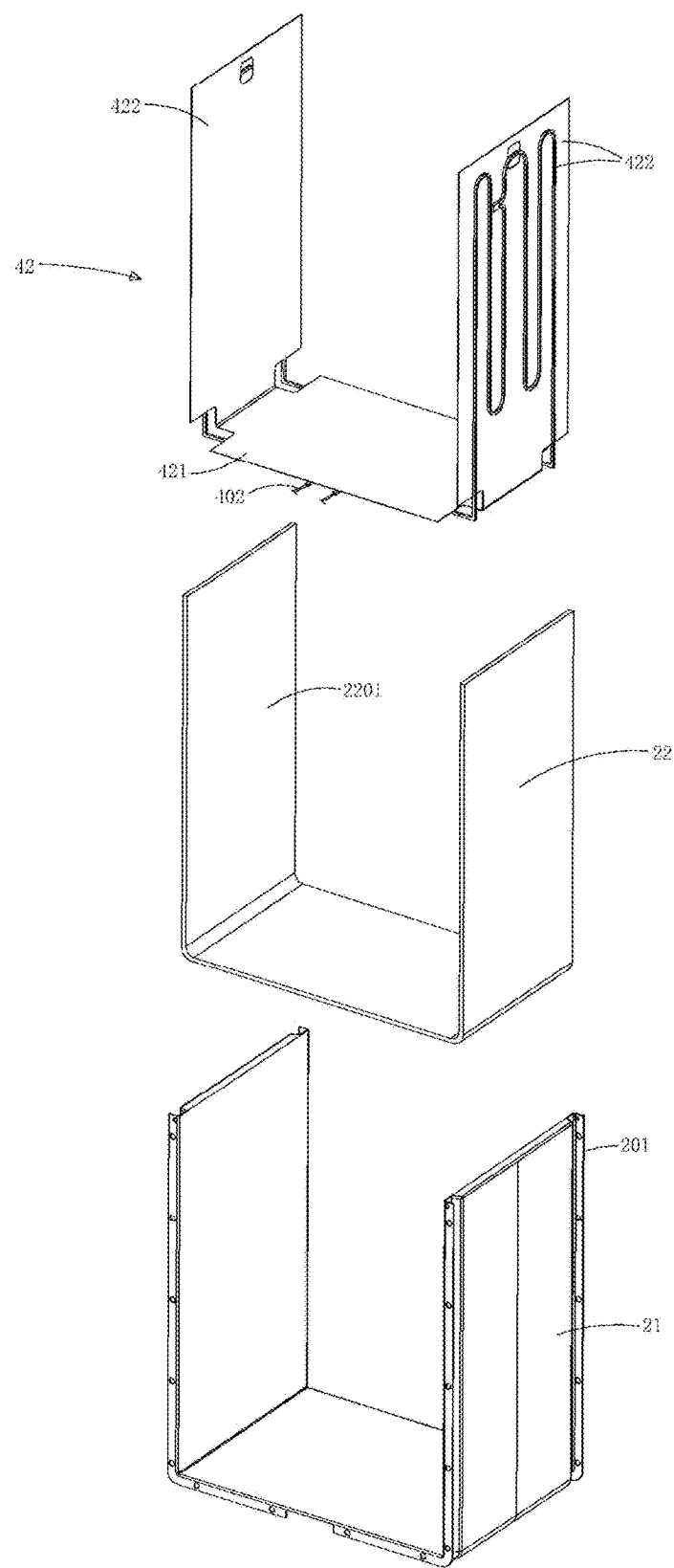
FIG. 11 is an exploded view of a first receiving bag, a first heat-insulation layer, and a flexible heating sheet according to an embodiment of the present disclosure.

Structures of the flexible heating sheet 42 is as shown in FIG. 11.

The flexible heating sheet 42 includes a bottom heating sheet 421 and two side heating sheets 422. The bottom heating sheet 421 is disposed in the flexible bottom plate 202. The two side heating sheets 422 are disposed in the two flexible side plates 203 respectively. The two side heating sheets 422 are both electrically connected to the bottom heating sheet 421. The bottom heating sheet 421 is electrically connected to the control board 43 via a second wire 402. The second wire 402 also extends through the wire through-slot 122 to be further connected to the control board 43. In summary, the configuration of the flexible heating sheet 42 and the two heating plates 41 enables the bottom wall 61 and the four side walls 62 of the receiving chamber 6 to generate heat. Therefore, a heating efficiency of the towel heating device is improved.

To be noted that the control board 43 controlling the two heating plates 41 and the flexible heating sheet 42 may be achieved by any controlling technology available in the art. Of course, any ordinary skilled person in the art shall understand that, a built-in power supply may be arranged on the shell body 11, or the control board 43 may be connected to an external power supply, such that power is provided for the heating plates 41 and the flexible heating sheet 42.

In addition, a display screen may be arranged on a front shell 101. The display screen is electrically connected to the control board 43. The display screen may be configured to display information about an operating state of the heating assembly 4. A plurality of control buttons for controlling the operating state of the heating assembly 4 may be arranged on the display screen. Alternatively, the operating state of the heating assembly 4 may be controlled remotely.

Figure 13:
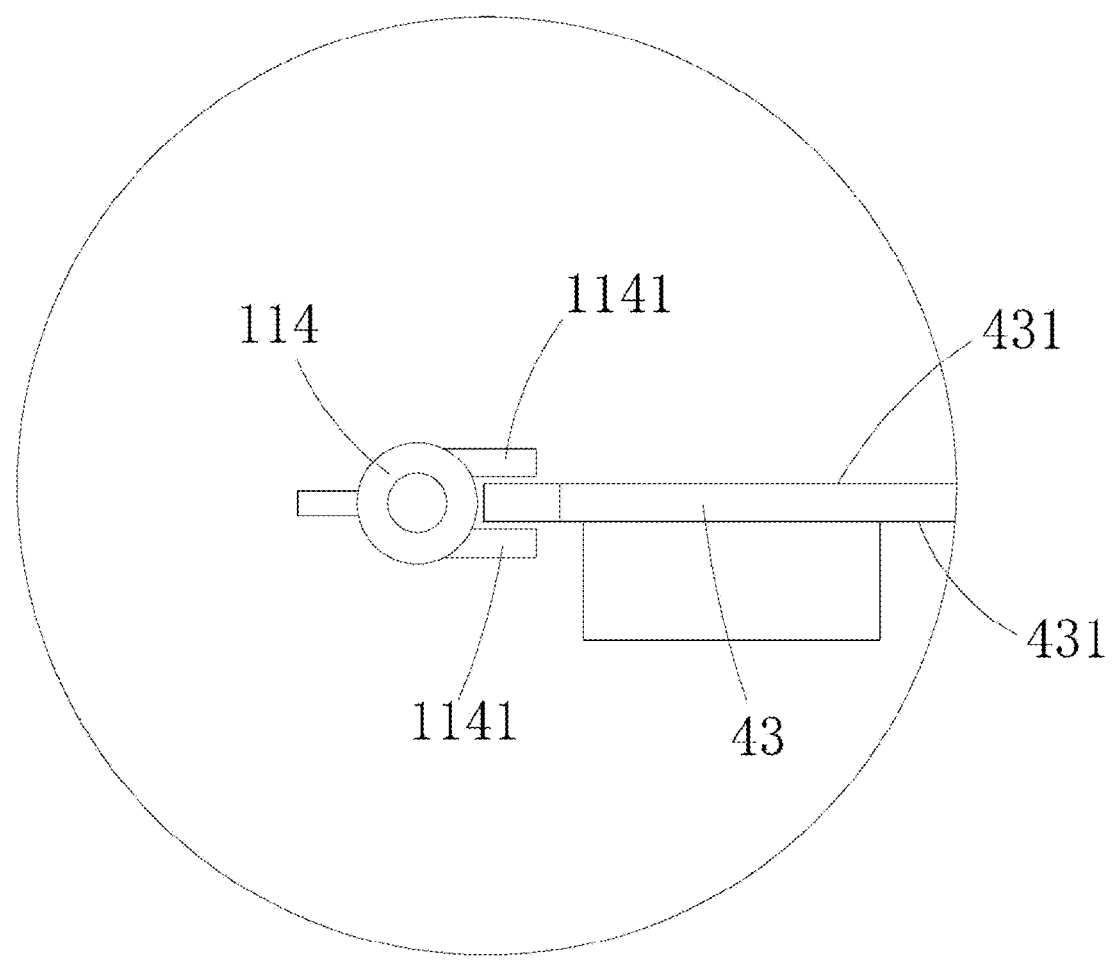
FIG. 13 is an enlarged view of a portion C shown in FIG. 12.

Mounting the control panel 43 to the rigid shell 1 is as shown in FIGS. 12 and 13.

At least two third positioning posts 114 are further arranged in the shell body 11. Each third positioning post 114 is arranged with two second clamping protrusions 1141. The two second clamping protrusions 1141 abut against two sides 431 of the control plate 43, respectively. The two second clamping protrusions 1141 cooperatively clamp the heating plate 41. All of the third positioning posts 114 cooperatively clamp the control plate 43, such that a balanced force is applied on the control plate 43. Of course, the user may disengage the control plate 43 from the plurality of third positioning posts 114 by pulling the control plate 43.

Further, in order to achieve heat preservation performance of the towel heating device, in the present embodiment, as shown in FIGS. 4 and 5, the flexible connection member 2 includes a first receiving bag 21 and a first heat-insulation layer 22. The flexible heating sheet 42 and the first heat-insulation layer 22 are arranged inside the first receiving bag 21. The first receiving bag 21 is arranged with two first connection portions 201 at an edge of the first receiving bag 21. To be noted that the first receiving bag 21 and the first heat-insulation layer 22 are layered structures of the flexible connection member 2. Combination of the first receiving bag 21 and the first heat-insulation layer 22 cooperatively form the above-mentioned flexible bottom plate 202 and the two flexible side plates 203.

The first heat-insulation layer 22 is made of heat-insulation cotton, and the first heat-insulation layer 22 is soft.

In the present embodiment, the first receiving bag 21 is formed by two first fabric sheets 211 sewn to each other. Both the flexible heating sheet 42 and the first heat-insulation layer 22 are sandwiched between the two first fabric sheets 211. Each first fabric sheet 211 is made of fabric material. The flexible heating sheet 42 is disposed on a side 2201 of the first heat-insulation layer 22 facing the receiving chamber 6. Therefore, the heat generated by the flexible heating sheet 42 passes through one of the two first fabric sheets 211 to be conducted to the receiving chamber 6, obstruction during heat conduction is reduced. In addition, due to a blocking effect of the first heat-insulation layer 22, the heat generated by the flexible heating sheet 42 cannot pass through the first heat-insulation layer 22 easily, and therefore, the heat is not easily conducted to an outside environment.

Specifically, the two first fabric sheets 211 are stitched together to each other at edges thereof. The first connection portion 201 is formed at a position where the two first fabric sheets 211 are stitched to each other. The first wire 401 and the second wire 402 both extend between the two first fabric sheets 211. In addition, holes may be pre-defined in the first receiving bag 21 to allow the first wire 401 and the second wire 402 to extend through the first receiving bag 21.

Further, in order to improve the heat preservation performance of the receiving chamber 6, in the present embodiment, as shown in the FIGS. 1, 2, 9, and 10, the towel heating device further includes a top cover 5. A first end of the top cover 5 is arranged with a second connection portion 503. The second connection portion 503 is clamped between the second fixation frame 13 and the shell body 11 of one of the two rigid shells 1. Furthermore, the second positioning posts 113 extend through the second connection portion 503, preventing the second connection portion 503 from being disengaged from the rigid shell 1. A second end 502 of the top cover 5 can swing around the second connection portion 503 and may be lapped on the other one of the two rigid shells 1, enabling the top cover 5 to cover the opening 7 and to improve sealing of the receiving chamber 6. In addition, a limiting tab 132 is arranged on the second fixation frame 13. The limiting tab 132 is extending towards the opening 7. The second end 502 of the top cover 5 may be lapped on the limiting tab 132.

In the present embodiment, the top cover 5 includes a second receiving bag 51 and a second heat-insulation layer 52. The second heat-insulation layer 52 is arranged inside the second receiving bag 51. The second receiving bag 51 extends at an edge 5101 to form a second connection portion 503. The second receiving bag 51 and the second heat-insulation layer 52 are both layered structures of the top cover 5. The second receiving bag 51 is formed by two second fabric sheets 511. The second heat-insulation layer 52 is sandwiched between the two second fabric sheets 511. The second heat-insulation layer 52 is made of heat-insulation cotton. When the top cover 5 covers the opening 7, a rate at which the heat inside the receiving chamber 6 is dissipated from the opening 7 is reduced, i.e., the heat-insulation performance of the receiving chamber 6 is improved.

Further, in the present embodiment, the two rigid shells 1 are distributed in a front-rear direction. One of the two rigid shells 1 is named as a front shell 101, and the other one of the two rigid shells 1 is named as a rear shell 102. The opening 7 is defined at the top of the flexible connection member 2. The two foldable brackets 3 are disposed at a left side and a right side of the towel heating device. This configuration is more conformity with usage habits of the user.

In an embodiment, as shown in FIG. 14, the front shell 101 is arranged with a first connection shaft 1011 and a second connection shaft 1012. The rear shell 102 is arranged with a third connection shaft 1021 and a fourth connection shaft 1022. The foldable bracket 3 includes a first support rod 31 and a second support rod 32. The first support rod 31 and the second support rod 32 are crossed to each other and are hinged to each other at a middle of the first support rod 31 and the second support rod 32. A first end 311 of the first support rod 31 defines a first slide slot 301, the first connection shaft 1011 slides in the first slide slot 301. A second end 312 of the first support rod 31 is rotationally connected to the fourth connection shaft 1022. A first end 321 of the second support rod 32 is rotationally connected to the second connection shaft 1012. A second end 322 of the second support rod 32 defines a third slide slot 303. The third connection shaft 1021 slides in the third slide slot 303. In the present embodiment, the above configuration provides a feasible structural basis for the foldable bracket 3 to move.

In another embodiment, as shown in FIG. 1, the front shell 101 is arranged with a first connection shaft 1011 and a second connection shaft 1012. The rear shell 102 is arranged with a third connection shaft 1021 and a fourth connection shaft 1022. The foldable bracket 3 includes a first support rod 31 and a second support rod 32. The first support rod 31 and the second support rod 32 are crossed to each other and are hinged to each other at a middle of the first support rod 31 and the second support rod 32. A first end 311 of the first support rod 31 defines a first slide slot 301, a second end 312 of the first support rod 31 defines a fourth slide slot 304. The first connection shaft 1011 slides in the first slide slot 301, the fourth connection shaft 1022 slides in the fourth slide slot 304. A first end 321 of the second support rod 32 defines a second slide slot 302, a second end 322 of the second support rod 32 defines a third slide 303. The second connection shaft 1012 slides in the second slide 302, and the third connection shaft 1021 slides in the third slide 303. In the present embodiment, the above configuration provides a feasible structural basis for the foldable bracket 3 to move. Compared to the above embodiment, the present embodiment enables a length of one slide slot to be shortened, effectively improving structural strength of the support rod.

Further, since the towel heating device usually needs to be placed in a bathroom, the floor is often wet or has moisture. Therefore, in the present embodiment, when the foldable bracket 3 is in the unfolded state, a lower end of the foldable bracket 3 is configured to be supported on the floor. That is, the first end 311 of the first support rod 31 and the second end 322 of the second support rod 32 contact the floor, enabling a bottom 1003 of the rigid shell 1 and a bottom 2001 of the flexible connection member 2 are both above the floor, preventing the rigid shell 1 and the flexible connection member 2 from becoming dirty due to contacting the floor.

It is understood that in other embodiments, the two rigid shells 1 may alternatively be distributed in an up-down direction, and the opening 7 is defined at the upper rigid shell 1. In this case, the flexible connection member 2 is an enclosed structure, and the flexible connection member 2 completely wraps the space between the two rigid shells 1. This embodiment is not shown in the accompanying drawings.

Obviously, the above-described embodiments show only some of, not all of, the embodiments of the present disclosure. All of the embodiments may be performed in combination with each other. The accompanying drawings show preferred embodiments of the present disclosure, but do not limit the scope of the present disclosure. The present disclosure may be achieved in various different forms. On the contrary, these embodiments are provided for the purpose for understanding the present disclosure more thoroughly and comprehensively. Although the present disclosure has been described in detail with reference to the foregoing embodiments, any ordinary skilled person in the art may still modify the technical solutions in the foregoing specific embodiments or make equivalent substitutions for some of the technical features therein. Any equivalent structure made based on the contents of the specification and the accompanying drawings of the present disclosure, applied directly or indirectly in other related technical fields, shall be equivalently included in scope of the present disclosure.

What is claimed is:

1. A foldable towel heating device, comprising:
   two rigid shells;
   a flexible connection member, connecting with the two rigid shells, wherein, the flexible connection member and the two rigid shells cooperatively enclose a receiving chamber; any one of the two rigid shells and the flexible connection member defines an opening communicating with the receiving chamber;
   two foldable brackets, connecting with the two rigid shells, wherein, when the two foldable brackets are being folded, the two rigid shells are driven to move to approach each other, the flexible connection member is driven to be folded correspondingly; and when the two foldable brackets are being unfolded, the two rigid shells are driven to move away from each other, the flexible connection member is driven to be unfolded correspondingly; and
   a heating assembly, disposed in the two rigid shells and/or the flexible connection member, wherein, the heating assembly is configured to heat the receiving chamber;
   wherein, the flexible connection member is arranged with two first connection portions, the two first connection portions are connected to the two rigid shells respectively; and each of the two rigid shells comprises a shell body and a first fixation frame, the first fixation frame is connected to the shell body, each first connection portion is clamped between the respective first fixation frame and the respective shell body.

2. The foldable towel heating device according to claim 1, wherein, the shell body is arranged with a plurality of first positioning posts, the first positioning posts extend through the first connection portion, and the first fixation frame is fastened, by bolts, to the plurality of the first positioning posts.

3. The foldable towel heating device according to claim 1, wherein, the first fixation frame is formed by a plurality of first fixation rods being successively connected to each other from end to end.

4. The foldable towel heating device according to claim 1, wherein, the rigid shell further comprises a second fixation frame, the second fixation frame is connected to the shell body, the heating assembly is mounted on the second fixation frame, the second fixation frame is disposed at an inner side of the first fixation frame, the first connection portion further passes through a gap between the first fixation frame and the second fixation frame.

5. The foldable towel heating device according to claim 4, wherein, the shell body is arranged with a plurality of second positioning posts, the plurality of second positioning posts are configured to be inserted into the second fixation frame, the second fixation frame is fastened to the plurality of second positioning posts by bolts.

6. The foldable towel heating device according to claim 4, wherein, the second fixation frame is an enclosed structure, the second fixation frame is formed by a plurality of second fixation rods successively connected to each other from end to end, the plurality of second fixation rods are cooperatively configured to fix the heating assembly.

7. The foldable towel heating device according to claim 5, further comprising a top cover, wherein, the top cover is movably mounted to one of the two rigid shells, and the top cover is configured to cover the opening.

8. The foldable towel heating device according to claim 7, wherein, a first end of the top cover is arranged with a second connection portion, the second connection portion is clamped between the second fixation frame and the shell body of one of the two rigid shells, the plurality of second positioning posts further extend through the second connection portion, the second end of the top cover is capable of swinging around the second connection portion, and the second end of the top cover is capable of being lapped to the other one of the two rigid shells.

9. The foldable towel heating device according to claim 8, wherein, the top cover comprises a second receiving bag and a second heat-insulation layer, the second heat-insulation layer is arranged inside the second receiving bag, the second connection portion is arranged on the second receiving bag.

10. The foldable towel heating device according to claim 8, wherein, the second fixation frame is arranged with a limiting tab, the limiting tab extends towards the opening, and the second end of the top cover is capable of being lapped on the limiting tab.

11. The foldable towel heating device according to claim 9, wherein, the second receiving bag comprises two second fabric sheets, the second heat-insulation layer is sandwiched between the two second fabric sheets.

12. The foldable towel heating device according to claim 11, wherein, the two second fabric sheets are stitched to each other at edges thereof to form the second connection portion.

13. The foldable towel heating device according to claim 1, wherein, the flexible connection member comprises a first receiving bag and a first heat-insulation layer, the first heat-insulation layer is arranged inside the first receiving bag, the first connection portion is disposed on the first receiving bag, the first receiving bag comprises two first fabric sheets, the first heat-insulation layer is sandwiched between the two first fabric sheets.

14. The foldable towel heating device according to claim 13, wherein, the two first fabric sheets are stitched to each other at edges thereof to form the first connection portion.

15. The foldable towel heating device according to claim 1, wherein, the two rigid shells are a front shell and a rear shell, the opening is located at a top of the flexible connection member, and each foldable bracket is a scissor-type structure.

16. The foldable towel heating device according to claim 1, wherein, when the two foldable brackets are unfolded, lower ends of the two foldable brackets are supported on the ground, and the two rigid shells and the flexible connection member are suspended from the ground.

17. A foldable towel heating device comprising:
two rigid shells;
a flexible connection member, connecting with the two rigid shells, wherein, the flexible connection member and the two rigid shells cooperatively enclose a receiving chamber; any one of the two rigid shells and the flexible connection member defines an opening communicating with the receiving chamber;
two foldable brackets, connecting with the two rigid shells, wherein, when the two foldable brackets are being folded, the two rigid shells are driven to move to approach each other, the flexible connection member is driven to be folded correspondingly; and when the two foldable brackets are being unfolded, the two rigid shells are driven to move away from each other, the flexible connection member is driven to be unfolded correspondingly; and
a heating assembly, disposed in the two rigid shells and/or the flexible connection member, wherein, the heating assembly is configured to heat the receiving chamber;
wherein, the two rigid shells are a front shell and a rear shell;
each of the two foldable brackets comprises a first support rod and a second support rod, the first support rod and the second support rod cross with and are hinged to each other at a middle of the first support rod and the second support;
a first end of the first support rod and a first end of the second support rod are rotatable with respect to the front shell; a second end of the first support rod and a second end of the second support rod are rotatable with respect to the rear shell; and
at least two of the first end of the first support rod, the first end of the second support rod, the second end of the first support rod, and the second end of the second support rod is slidably connected to at least one of the two rigid shells;
wherein the front shell is arranged with a first connection shaft and a second connection shaft, and the rear shell is arranged with a third connection shaft and a fourth connection shaft;
the first end of the first support rod defines a first slide slot, the second end of the first support rod defines a fourth slide slot, the first connection shaft is slidable in the first slide slot, the fourth connection shaft is slidable in the fourth slide slot;
the first end of the second support rod defines a second slide slot, the second end of the second support rod defines a third slide slot, the second connection shaft is slidable in the second slide slot, and the third connection shaft is slidable in the second third slot.

18. A foldable towel heating device comprising:
two rigid shells;
a flexible connection member, connecting with the two rigid shells, wherein, the flexible connection member and the two rigid shells cooperatively enclose a receiving chamber; any one of the two rigid shells and the flexible connection member defines an opening communicating with the receiving chamber;
two foldable brackets, connecting with the two rigid shells, wherein, when the two foldable brackets are being folded, the two rigid shells are driven to move to approach each other, the flexible connection member is driven to be folded correspondingly; and when the two foldable brackets are being unfolded, the two rigid shells are driven to move away from each other, the flexible connection member is driven to be unfolded correspondingly; and
a heating assembly, disposed in the two rigid shells and/or the flexible connection member, wherein, the heating assembly is configured to heat the receiving chamber;
wherein, the two rigid shells are a front shell and a rear shell;
each of the two foldable brackets comprises a first support rod and a second support rod, the first support rod and the second support rod cross with and are hinged to each other at a middle of the first support rod and the second support;
a first end of the first support rod and a first end of the second support rod are rotatable with respect to the front shell; a second end of the first support rod and a second end of the second support rod are rotatable with respect to the rear shell; and at least two of the first end of the first support rod, the first end of the second support rod, the second end of the first support rod, and the second end of the second support rod is slidably connected to at least one of the two rigid shells;

wherein the front shells is arranged with a first connection shaft and a second connection shaft, and the rear shell is arranged with a third connection shaft and a fourth connection shaft;

the first end of the first support rod defines a first slide slot, the first connection shaft is slidable in the first slide slot, the second end of the first support rod is rotationally connected to the fourth connection shaft; and the first end of the second support rod is rotationally connected to the second connection shaft, the second end of the second support rod defines a third slide slot, the third connection shaft is slidable in the second third slot.

* * * * *